United States Patent
Steer

(10) Patent No.: US 12,376,985 B2
(45) Date of Patent: Aug. 5, 2025

(54) WASTE MANAGEMENT APPLIANCE

(71) Applicant: ProSys International Limited, London (GB)

(72) Inventor: Graham Steer, London (GB)

(73) Assignee: Prosys International Limited, London (GB)

( * ) Notice: Subject to any disclaimer, the term of this patent is extended or adjusted under 35 U.S.C. 154(b) by 967 days.

(21) Appl. No.: 17/486,212

(22) Filed: Sep. 27, 2021

(65) Prior Publication Data
US 2022/0008241 A1 Jan. 13, 2022

Related U.S. Application Data

(63) Continuation of application No. PCT/EP2020/058331, filed on Mar. 25, 2020.

(30) Foreign Application Priority Data

Mar. 26, 2019 (GB) ..................................... 1904193

(51) Int. Cl.
| | | |
|---|---|---|
| *A61F 5/451* | (2006.01) | |
| *A61F 5/44* | (2006.01) | |
| *A61M 3/02* | (2006.01) | |
| *A61M 25/10* | (2013.01) | |

(52) U.S. Cl.
CPC ............ *A61F 5/451* (2013.01); *A61F 5/4405* (2013.01); *A61M 3/0295* (2013.01);
(Continued)

(58) Field of Classification Search
CPC .. A61M 2025/1084; A61M 2025/1081; A61M 2025/1075; A61M 3/0295;
(Continued)

(56) References Cited

U.S. PATENT DOCUMENTS

| | | | | |
|---|---|---|---|---|
| 3,127,893 A | * | 4/1964 | Montague | ........... A61M 3/0279 604/275 |
| 3,938,521 A | | 2/1976 | Ritota et al. | |

(Continued)

FOREIGN PATENT DOCUMENTS

| | | |
|---|---|---|
| EP | 1514572 A2 | 3/2005 |
| EP | 1547639 A2 | 6/2005 |

(Continued)

OTHER PUBLICATIONS

PCT Written Opinion and The International Search Report, Intl. App. No. PCT/EP/2020/058331, dated Nov. 11, 2020, 20 pages.

*Primary Examiner* — Sarah Al Hashimi
*Assistant Examiner* — Arjuna P Chatrathi
(74) *Attorney, Agent, or Firm* — Barley Snyder

(57) ABSTRACT

A waste management appliance includes a tubular body having a proximal end and a distal end, a cowl fastened to the tubular body at a first circumferential location in a vicinity of the proximal end, a balloon provided within the cowl, and an inflation lumen opening to an interior of the balloon and extending toward the distal end of the tubular body. The cowl extends outside of the tubular body to a second circumferential location spaced from the first circumferential location and is fastened to the tubular body at the second circumferential location. The balloon is inflatable to a desired extent within the cowl by injecting a predetermined amount of fluid into the balloon via the inflation lumen; the cowl restrains inflation of the balloon beyond the desired extent in the event of an injection of more than the predetermined amount of fluid into the balloon.

18 Claims, 4 Drawing Sheets

(52) U.S. Cl.
CPC .............. *A61M 25/10182* (2013.11); *A61M 25/10184* (2013.11); *A61M 25/10186* (2013.11); *A61M 2025/1081* (2013.01); *A61M 2202/068* (2013.01); *A61M 2205/0222* (2013.01); *A61M 2205/0238* (2013.01); *A61M 2210/1067* (2013.01)

(58) Field of Classification Search
CPC .......... A61M 25/10184; A61M 3/0279; A61M 3/0291; A61M 3/0287; A61M 3/027; A61M 5/451; A61M 5/442; A61M 2025/0177; A61M 25/0102; A61M 25/0111; A61M 25/013; A61M 2025/02687; A61M 2025/0681

See application file for complete search history.

(56) References Cited

U.S. PATENT DOCUMENTS

| | | | | |
|---|---|---|---|---|
| 2004/0106901 | A1* | 6/2004 | Letson | A61M 25/10 604/910 |
| 2005/0054996 | A1* | 3/2005 | Gregory | A61F 5/442 604/317 |
| 2005/0137526 | A1* | 6/2005 | Machado | A61M 25/01 604/102.01 |
| 2005/0177104 | A1* | 8/2005 | Conway | A61M 25/1036 604/103.05 |
| 2006/0271091 | A1* | 11/2006 | Campbell | A61M 25/104 606/192 |
| 2011/0282311 | A1* | 11/2011 | Nishtala | A61F 5/4405 604/332 |
| 2012/0136324 | A1* | 5/2012 | Hanuka | A61F 5/441 604/318 |
| 2014/0107572 | A1* | 4/2014 | Jin | A61M 25/10186 604/99.01 |
| 2015/0112312 | A1* | 4/2015 | Mooney | A61M 25/10182 604/544 |
| 2018/0229013 | A1* | 8/2018 | Tsai | A61M 25/10187 |

FOREIGN PATENT DOCUMENTS

| | | | | |
|---|---|---|---|---|
| EP | 2862592 | A1 | 4/2015 | |
| GB | 2516429 | A * | 1/2015 | ............. A61F 5/445 |
| WO | 2011100187 | A1 | 8/2011 | |
| WO | 2013074763 | A1 | 5/2013 | |

* cited by examiner

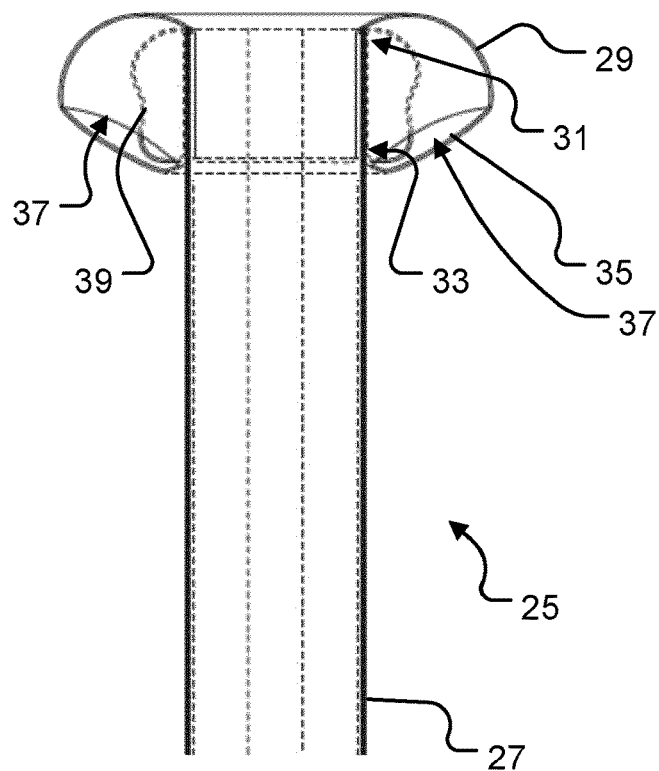
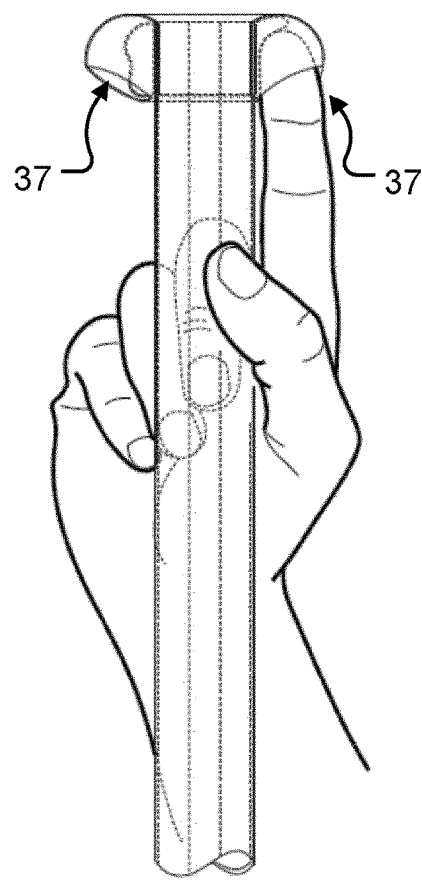
FIG. 3
FIG. 4
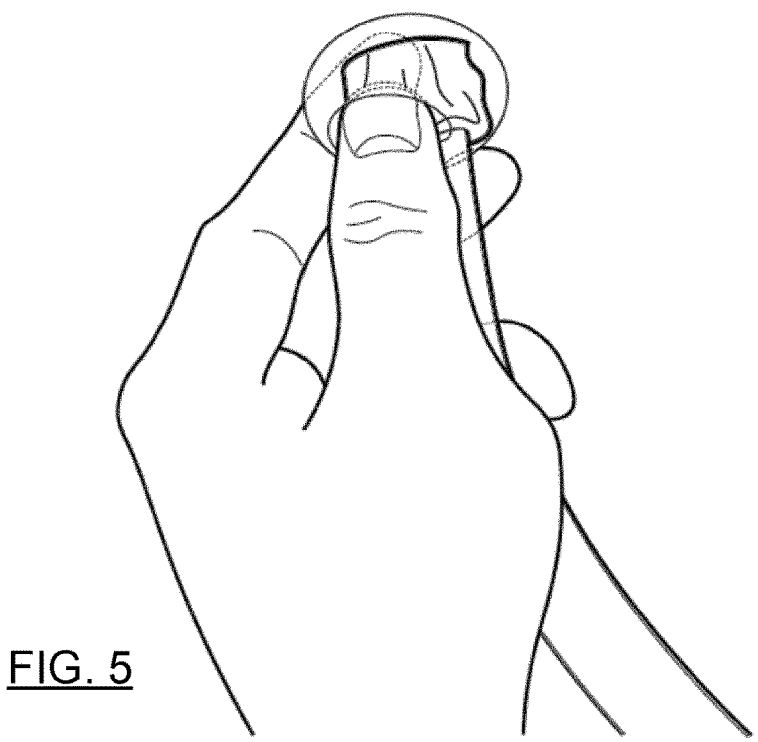
FIG. 5

WASTE MANAGEMENT APPLIANCE

CROSS-REFERENCE TO RELATED APPLICATIONS

This application is a continuation of PCT International Application No. PCT/EP2020/058331, filed on Mar. 25, 2020, which claims priority under 35 U.S.C. § 119 to Great Britain Patent Application No. 1904193.8, filed on Mar. 26, 2019.

FIELD OF THE INVENTION

This invention relates to waste management appliances, particularly but not exclusively to waste management appliances—and more particularly to so-called balloon catheters—that can be inserted into the rectum or stoma of a subject.

BACKGROUND

It has long been understood that appliances that are to be inserted into a subject's body should preferably be soft and pliable in order to avoid discomfort for the subject. For example, the Foley catheter was developed in 1937 and comprised a latex rubber catheter that was designed for insertion into the bladder via a subject's urethra. The catheter comprises a tube with an opening at the distal end (through which urine can flow when the catheter is in place), and a balloon that is inflated (via a lumen built into the tube) once the balloon is inside the bladder to hold the catheter in place.

More recent incarnations of the Foley catheter have been made from silicone, and in general terms it is fair to state that it is now well understood that subject comfort will be enhanced by increasing the softness and pliability of at least that part of the device that is inserted into the subject.

However, there is a limit to how soft and pliable such devices can be, as medical practitioners need the device to be sufficiently rigid to enable it to be inserted into the subject. Thus, there is a happy medium to be struck between increasing softness to enhance subject comfort and ensuring the device is sufficiently rigid that it can easily be inserted into the subject.

One attempt to provide such a happy medium is disclosed in European Patent No. 1547639. This patent discloses a rigid insertion tool, and a separate balloon catheter waste management appliance (for use with the tool) that has a distal end which is formed entirely of soft, compliant material and includes a positioning pocket provided between the balloon and the catheter tube. The insertion tool can be inserted into the pocket to facilitate insertion of the catheter into the patient. The intention with this arrangement is that as the necessary rigidity (for insertion) is provided by the tool, the device itself can be extremely soft and compliant (presumably so much so that it cannot readily be inserted into the subject without the tool).

Whilst this arrangement would appear to provide the abovementioned "happy medium", there are significant drawbacks associated with it. For example, it is never advisable to insert rigid tools into a subject, and in the context of fecal management, a rigid insertion tool in the hands of a careless or inexperienced practitioner could easily cause a perforation of the subject's bowel. It is also the case that as the tool is separate from the waste management device, there is always the potential for tools to be inadvertently (or deliberately) reused between patients. A further drawback is that as the system has a separate tool, use of the system is no longer intuitive, and users will need to be instructed in how to properly use the system. In addition, as the catheter includes only a single positioning pocket, it can be difficult for practitioners to access the pocket for inserting the catheter without twisting the catheter tube. Lastly, a multi-part system will invariably be significantly more expensive than traditional waste management appliances, thereby increasing patient care costs (particularly as the catheter will need to be changed on a regular basis).

Another issue associated with balloon catheters is that of over-inflation of the balloon once the catheter has been inserted into a patient. For example, fecal management systems using an inflated balloon to retain the catheter in the patient must be used carefully because they can create too much pressure on the rectal tissue if the balloon (which functions to retain the catheter in the rectum) is over inflated. That pressure is a result of the balloon being filled with a volume of fluid greater than the space available in the body cavity, and can result in damage (such as tissue necrosis) to the soft tissue surrounding the balloon.

WO2013074763 seeks to address this issue by providing a complex indicator mechanism that is coupled to the inflation lumen and a return lumen and is configured so that an indicator becomes visible through a viewing window in the indicator mechanism when the balloon has been correctly inflated. Whilst this arrangement enables practitioners to check whether a balloon has already been inflated, it doesn't actually prevent the balloon from being over-inflated, as over-inflation will simply cause the viewing window to bulge outwards. The arrangement disclosed in this application also requires the catheter to include an inflation lumen and a return lumen, both of which are coupled to the balloon at one end of the lumen and to the indicator mechanism at the other, thereby complicating construction of the catheter.

Aspects of the present invention have been devised with the foregoing issues in mind.

SUMMARY

In an embodiment, there is provided a waste management appliance comprising: a tubular body having proximal and distal ends; a balloon coupled to the tubular body in the vicinity of the proximal end thereof; an inflation lumen opening at a proximal end to the interior of said balloon and extending distally from the balloon towards the distal end of the tubular body, and a valve assembly fluidly coupled to a distal end of the inflation lumen, the valve assembly comprising a valve body having first and second valve chambers in fluid communication with said inflation lumen, a coupling for connecting the lumen to a source of fluid being provided in said first chamber, and a pressure relief valve being provided in said second chamber; the arrangement being such that forcing fluid into said lumen via said coupling from a source of fluid inflates said balloon until the balloon and lumen contain a predetermined quantity of fluid, whereupon continued forcing of fluid into said lumen causes said pressure relief valve to operate and fluid to leak from the lumen via said valve instead of further inflating said balloon.

An advantage of this arrangement is that attempts to over-inflate the balloon will automatically cause the valve assembly to operate and excess fluid to flow out of the valve assembly instead of into the balloon. This arrangement greatly reduces the risk of the balloon being overinflated and the concomitant risk to the health of the subject in which the appliance is inserted.

In accordance with a presently preferred embodiment of another aspect of the present invention, there is provided a waste management appliance, comprising: a tubular body having a proximal end and a distal end; a cowl fastened to said tubular body at a first circumferential location in the vicinity of said proximal end, said cowl extending distally outside of said tubular body to a second circumferential location spaced distally from said first circumferential location, said cowl being fastened to said tubular body at said second circumferential location at a plurality of spaced positions around the circumference of said tubular body; an inflatable balloon provided within said cowl; and an inflation lumen having a proximal end opening to the interior of said balloon and extending distally towards the distal end of said tubular body; wherein the cowl can be separated from said tubular body at a plurality of circumferential regions where the cowl is not fastened to the tubular body to form a plurality of pockets between the cowl and the uninflated balloon into any of which a finger can be inserted for the purpose of guiding the balloon into a subject, and the balloon can be inflated to a desired extent within the cowl by injecting a predetermined amount of fluid into said balloon via said lumen, the cowl functioning in the event of an attempt to inject more than said predetermined amount of fluid into said balloon to restrain inflation of said balloon beyond said desired extent.

This arrangement has two principal advantages. Firstly, the cowl provides a number of finger pockets to ease insertion of the appliance into a subject. Secondly, the cowl provides an effective way to restrain over-inflation of the balloon in the event that an attempt should be made to insert more than the predetermined quantity of fluid into the balloon. Finally, as the balloon expands into the cowl and ultimately contacts an internal surface of the cowl, so the force required to inject fluid into the balloon will greatly increase, thereby indicating to the person inflating the balloon that the balloon has been inflated to the required degree.

The waste management appliance may further comprises a valve assembly fluidly coupled to the inflation lumen, the valve assembly comprising a valve body having first and second valve chambers in fluid communication with said inflation lumen, a coupling for connecting the lumen to a source of fluid being provided in said first chamber, and a pressure relief valve being provided in said second chamber; the arrangement being such that the insertion of fluid into said lumen via said coupling from a source of fluid inflates said balloon until the balloon and lumen contain a predetermined quantity of fluid, whereupon continued insertion of fluid causes said pressure relief valve to operate and fluid to leak from the lumen via said valve instead of further inflating said balloon.

The pressure relief valve may comprise a valve member biased to prevent the flow of fluid from said lumen. The valve member may be biased by a resilient biasing means, for example a spring. The valve member may be biased by a biasing force in the region of 5 to 35 kPa, more preferably in the region of 15 to 20 kPa, and most preferably in the region of 16 to 18 kPa.

The tubular body may include an externally accessible irrigation lumen that opens proximate said proximal end of said tubular body.

The appliance may further comprise a waste collection receptacle. The appliance may comprise means for detachably mounting said receptacle to said distal end of said tubular body. The receptacle mounting means may comprise a plate with an opening, and means for attaching said distal end of said tubular body to said plate, in alignment with said plate opening.

Preferably at least part of said waste management appliance is provided with a lubricious coating. An internal surface of said tubular body and an external surface of said cowl may include a lubricious coating. The lubricious coating may comprise parylene.

Other features, advantages and embodiments of the invention are set out hereafter and in the dependent claims.

BRIEF DESCRIPTION OF THE DRAWINGS

Various aspects of the teachings of the present invention, and arrangements embodying those teachings, will hereafter be described by way of illustrative example with reference to the accompanying drawings, in which:

FIG. 3 is a schematic diagram of a waste management appliance according to an embodiment;

FIG. 4 is a schematic diagram of a use of the waste management appliance;

FIG. 5 is another schematic diagram of a use of the waste management appliance;

DETAILED DESCRIPTION OF THE EMBODIMENT(S)

Figure 1:
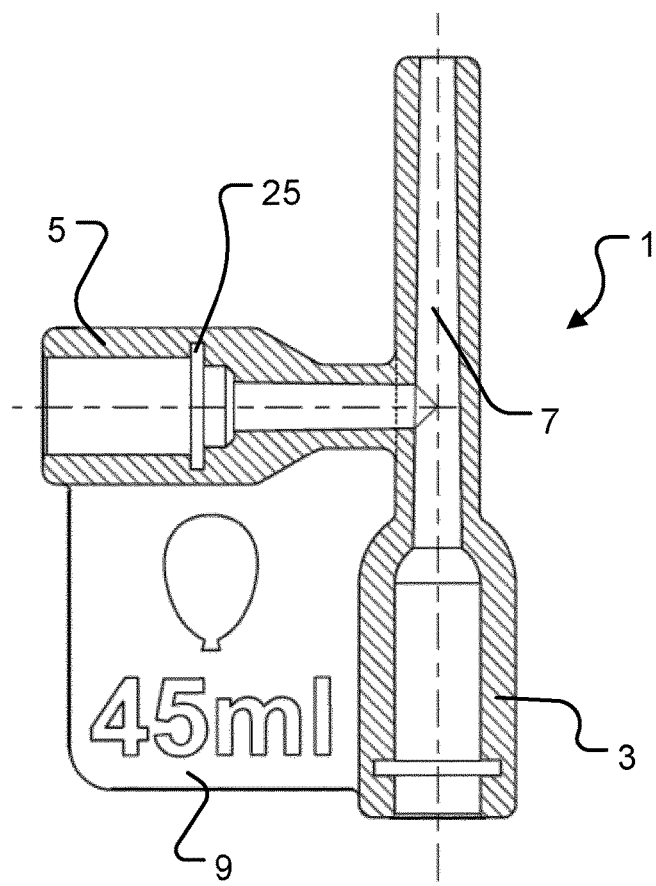
FIG. 1 is a sectional side view of a valve assembly according to an embodiment.

Particular reference will be made hereafter to waste management appliances that are configured for insertion into the rectum of a subject, i.e. for use as rectal catheters. It should be noted, however, that this particular application is merely illustrative, and that the appliances disclosed herein could be inserted into any body cavity for waste management purposes. For example, appliances of the type disclosed could be inserted into a stoma for waste management purposes.

As mentioned above, waste management appliances for insertion into the rectum or a stoma are well known and typically have a number of components in common. Typically, appliances for insertion into the rectum or a stoma comprise a tubular body through which waste material can pass, and an inflatable balloon that functions to retain the tubular body in the rectum or stoma of the subject. The inflatable balloon is typically toroidal in nature and is fastened to the tubular body (so as to surround the tubular body) at or near a proximal end of the tubular body.

A distal end of the tubular body is typically configured so that it can be coupled to a waste collection receptacle, such as a waste storage bag. For example, coupling means or receptacle mounting means may be provided to detachably couple the tubular element to the bag. The coupling means may comprise, in one implementation, a plate to which the distal end of the tubular element can be attached, and the bag can be detachably coupled to the plate so that waste from the tube can pass through an aperture in the plate and into the bag. In an embodiment, the coupling between the bag and plate may be configured to allow the bag to rotate relative to the plate so that the orientation of the bag relative to the plate can readily be adjusted. The plate may also be configured so that it can be attached to a subject's bed below the patient so that waste can flow from the patient under gravity into the bag.

In common with all other such appliances, the balloon is inflatable by a lumen that extends along the length of the tubular body from the balloon towards the distal end of the tube. The lumen may be incorporated into the wall of the tubular body or attached (wholly or at spaced locations) thereto. If attached to the wall, the lumen can extend inside the tubular body. Typically, the lumen terminates distally at a coupling, such as a luer lock, that enables the lumen to be coupled to a source of fluid (such as a syringe) that can be operated to force fluid into the lumen and thereby inflate the balloon.

The tubular body may also include (as is conventional with such appliances) an irrigation lumen, opening inside the tubular body proximate the proximal end of the tubular body, by which a practitioner can irrigate the subject's body cavity, for example to attempt to remove any blockages that might occur.

All of these aforementioned features are commonplace in the field of waste management appliances, in particular in the field of so-called balloon catheters, and as a consequence—for efficacy—will not be described in detail herein.

FIG. 1 shows, partly in section, a valve assembly 1 that can either be configured, as shown, as a discrete component for connection to a distal end of an inflation lumen of a waste management appliance, or be formed as an integral component of such a lumen (at the distal end thereof).

The valve assembly 1 defines a first hollow chamber 3 that is configured and arranged to accommodate a coupling for connecting the valve assembly 1 to a source of fluid. In one envisaged arrangement, the first assembly is configured to accommodate a luer lock coupling that can be connected to a suitable syringe (which provides a source of fluid for injection into the inflation lumen).

The valve assembly 1 also defines a second hollow chamber 5 that is configured to accommodate a pressure-relief valve that enables excess injected fluid to escape from the inflation lumen, to thereby avoid overinflating the balloon.

The first and second hollow chambers 3, 5 each open to a hollow channel 7 that fluidly connects to the inflation lumen (either by virtue of being part of that lumen, or on account of being connected to that lumen).

In an embodiment, the first and second chambers 3, 5 are set at approximately 90 degrees to one another, and a webbing 9 is provided between external walls of the chambers 3, 5 on which information can be provided as shown in FIG. 1 (in this instance the volume of fluid (45 ml) that should be injected into the inflation lumen to properly inflate the balloon). In an embodiment, the valve assembly 1 is formed of silicone.

Figure 2:
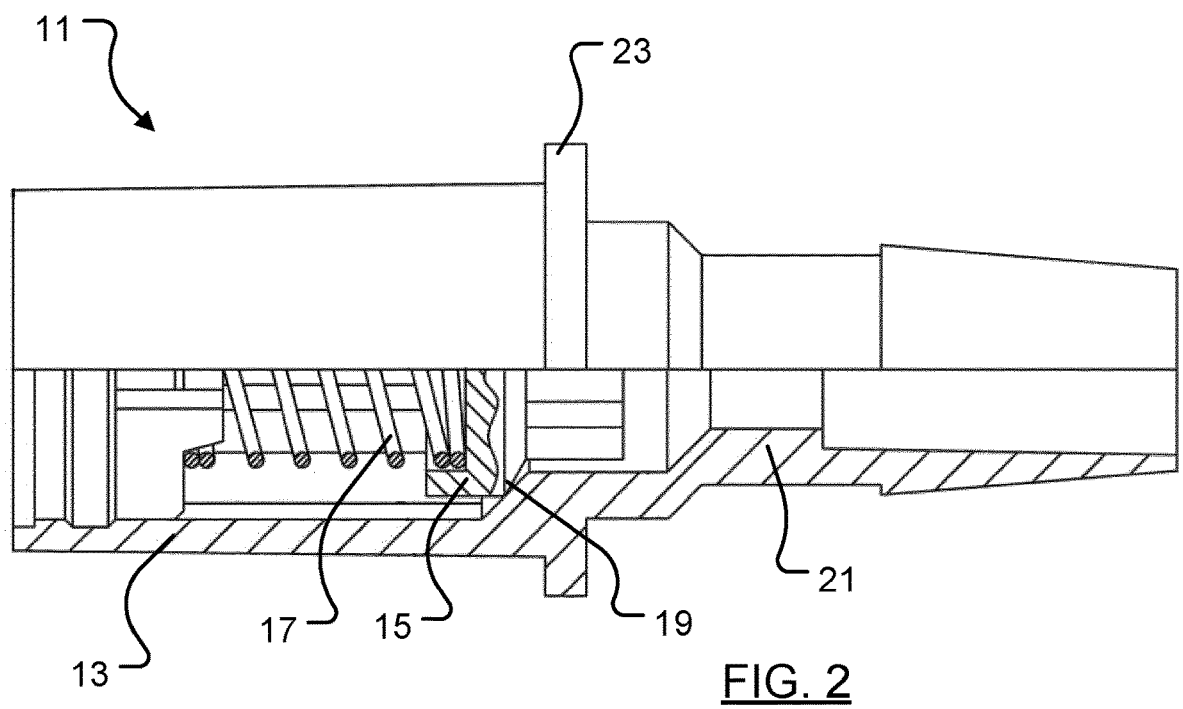
FIG. 2 is a partly sectional side view of a valve of the valve assembly.

FIG. 2 is a schematic representation, partly in section, of an illustrative pressure-relief valve 11 that is configured to be accommodated within the aforementioned second chamber 5 of the valve assembly 1. The valve 11 comprises a main shank 13 within which a biased valve member 15 is provided. The valve member 15 is resiliently biased (in this instance by a spring 17) to bear against a valve seat defined by an internal wall 19 of the shank 13, which seat separates the shank 13 from a radially narrower nozzle 21 that provides a passage for fluid egress from the lumen when the pressure relief valve 11 is accommodated within the second chamber 5 of the valve assembly 1. To enhance retention of the valve 11 within the valve assembly 1, the shank 13 is provided with an external circumferential tab 23 in the vicinity of said valve seat 19 that mates with a complementary internal circumferential channel 25 in the second chamber 5 of the valve assembly 1 when the valve 11 is push fitted into the second chamber 5. In arrangements where the valve assembly 1 is of silicone, the second chamber 5 is capable of resiliently expanding in a radially outward direction as the valve 11 is pushed into the chamber 5 until the tab 23 locates in the channel 25, whereupon the second chamber 5 radially contracts to retain the valve 11 in the chamber 5.

In use, with a pressure relief valve 11 accommodated in the second chamber 5 and a suitable coupling (for example a luer lock coupling) in the first chamber 3, a source of fluid (such as a syringe) can be coupled to the coupling and fluid from the fluid source can be injected via the coupling in the first chamber 3 into the inflation lumen, and via the lumen into the balloon in the vicinity of the proximal end of the tubular body. As fluid is injected, the balloon inflates until a predetermined amount of fluid has been injected (in this instance 45 ml) and the balloon is fully inflated.

Once the balloon has been fully inflated, attempted injection of yet more fluid into the lumen (and thus the balloon) creates a back pressure that causes the valve member 15 to move against the bias of, in this instance, the spring 17 away from the valve seat 19. Once the valve member 15 has moved away from the valve seat 19, fluid can pass from the lumen through the nozzle 21, past the valve member 15, through the shank 13 and out of the valve assembly 1 to relieve the pressure within the lumen and thereby avoid significant unwanted expansion of the balloon (it being understood by persons skilled in the art that the balloon may expand very slightly until the biasing force on the valve member 15 is exceeded by the force exerted on the valve member 15 by the fluid within the lumen, but such slight expansion is not likely to be of significance insofar as the subject's wellbeing is concerned). To limit the extent of this slight additional expansion, the biasing force is in the range of 5 to 35 kPa, in the range of 15 to 20 kPa, or in the range of 16 to 18 kPa.

It can be seen from the foregoing, that this arrangement provides an elegantly simple way to reduce the chance of a patient being injured by an over-inflation of an inserted balloon catheter, and does so without requiring additional lumens of the type required by the previously proposed arrangement disclosed in WO2013074763. Attempts to over-inflate the balloon will automatically cause the valve assembly 1 to operate and excess fluid to flow out of the valve assembly 1 instead of into the balloon. This arrangement greatly reduces the risk of the balloon being overinflated and the concomitant risk to the health of the subject in which the appliance is inserted.

Referring now to FIG. 3 of the drawings there is depicted a proximal part of a waste management appliance 25 that provides advantages over the arrangements disclosed in both of the aforementioned previously proposed arrangements, irrespective of whether it is used in conjunction with the valve assembly disclosed above, or separately from that valve assembly. As such, it should be noted that the scope of the present invention extends to encompass the waste management appliance 25 described below on its own, as well as in combination with the valve assembly 1 described above.

The waste management appliance 25 comprises a tubular body 27 having a proximal end (shown in FIG. 4) and a distal end. The appliance 25 may include any of the features described above as being conventional for waste management appliances of this type.

As shown in FIG. 4, the tubular body 27 is provided with a cowl 29 that is coupled directly to the tubular body 27, in this particular instance at spaced circumferential locations on an outside surface of the tubular body 27, namely at a first location 31 proximate to the proximal end of the tubular body 27 (for example, at the proximal end of the tubular body 27) and at a second location 33 spaced distally from the first location 31.

In the shown embodiment, the cowl 29 is fastened (e.g. adhered) to the tubular body 27 around the entire external circumference of the tubular body 27 at the first circumferential location 31 proximate the proximal end of the tubular body 27, but only fastened to the tubular body 27 at spaced locations around the circumference of the tubular body 27 at the second circumferential location 33 so as to provide a plurality of locations 35 (in particular at least two, as depicted) around the circumference of the tubular body 27 at which the cowl 29 can be separated from the tubular body 27 to form a plurality of finger pockets 37.

In the shown embodiment, the cowl 29 may be cut-away (so as to be thinner in a proximal—distal direction) in those locations 35 where the cowl 29 is not affixed to the tubular body 27.

As illustrated schematically in FIGS. 4 and 5, an advantage of this arrangement is that a gloved finger or thumb can be inserted into one of the aforementioned finger pockets 37 for the purpose of manually easing the waste management appliance 25 into the subject.

Advantageously, as compared with the arrangement disclosed in EP1547639, the appliance 25 herein disclosed provides a plurality of finger pockets 37, any one of which can be used to ease insertion of the appliance 25 into the subject, the effect of which is that the likelihood of the tubular body 27 inadvertently being twisted as the appliance 25 is inserted (thereby potentially impeding the flow of waste from the subject) is greatly reduced.

In an envisaged alternative arrangement, the cowl 29 may be fastened (e.g. adhered) to an internal surface of the tubular body 27 in the vicinity of the first location 31 so that the cowl 29 extends proximally out from the proximal end of the tubular body 27. An advantage of this arrangement is that the cowl 29 would then cover the proximal end of the tubular body 27 and any rough edges of that proximal end.

As shown in FIG. 3, the appliance 25 includes a balloon 39 (shown deflated) that is provided within the cowl 29 in the vicinity of the proximal end of the tubular body 27, in this instance at the proximal end of the tubular body 27. The balloon 39 can be inflated via an inflation lumen once the appliance 25 has been inserted into a subject to retain the appliance in place. As shown in FIG. 4, the person inserting the appliance 25 can insert their finger into the cowl 29 and in between the cowl 29 and the balloon 39 to guide the appliance 25 as it is inserted into the subject.

As the balloon 39 is provided within the cowl 29, the cowl 29 functions—in addition to facilitating insertion of the appliance 25 into a subject—to resist over-inflation of the balloon 39. Specifically, as the balloon 39 is inflated so it will expand towards the cowl 29 until it occupies substantially all of the space between the cowl 29 and the outside of the tubular body 27, whereupon the cowl 29 will restrain further inflation of the balloon 39. It is also the case that as the balloon 39 comes into contact with the cowl 29, the force required to insert fluid into the balloon 39 will greatly increase, thereby signaling the person inflating the balloon 39 that it has been inflated to the required degree and should not be further inflated.

Whilst the arrangement 25 disclosed above is advantageous in its own right, it will be appreciated by persons skilled in the art that when this arrangement 25 is used in conjunction with the valve assembly 1 described above, the resulting appliance is particularly effective at reducing the likelihood of the balloon 39 being over-inflated.

Figure 6:
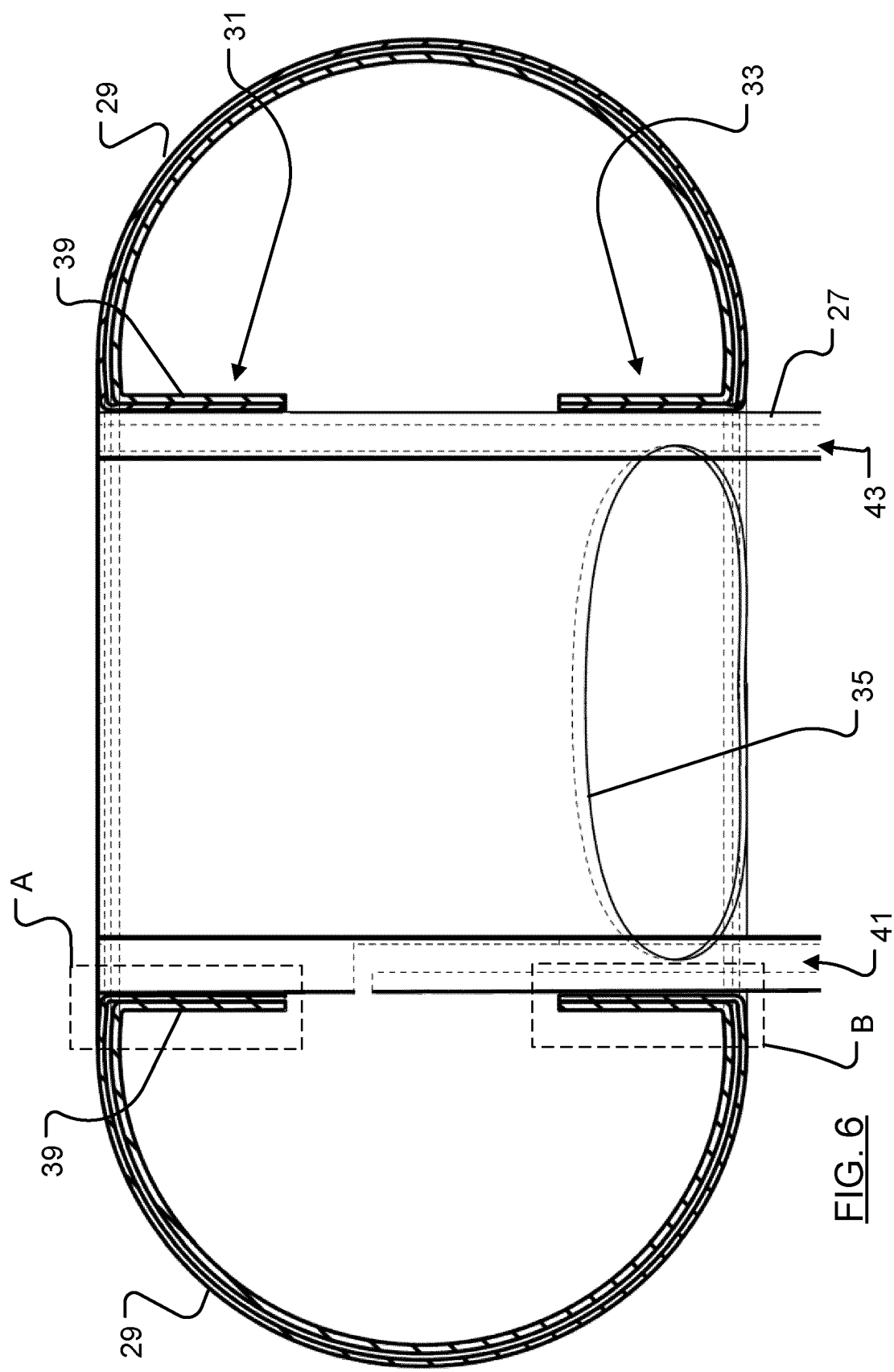
FIG. 6 is a sectional side view of a portion of the waste management appliance.
Figure 7:
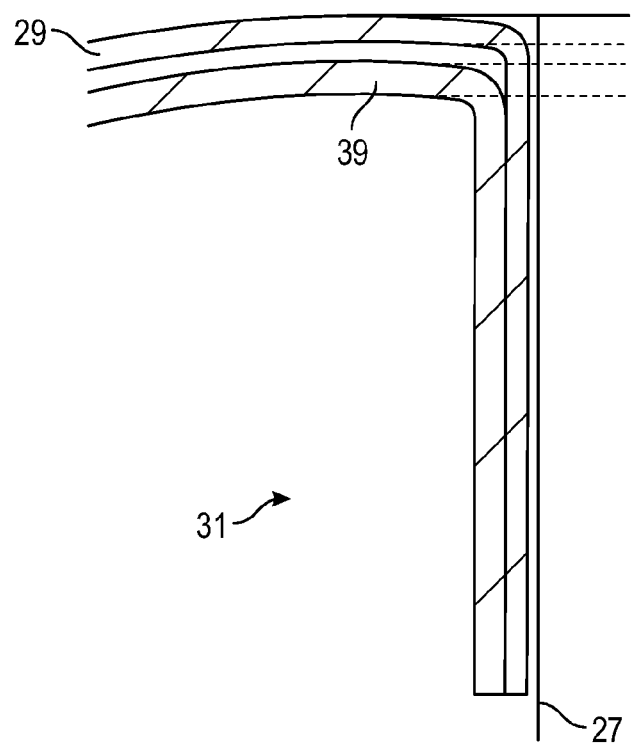
FIG. 7 is an enlarged sectional side view of a region A of the waste management appliance of FIG. 6.
Figure 8:
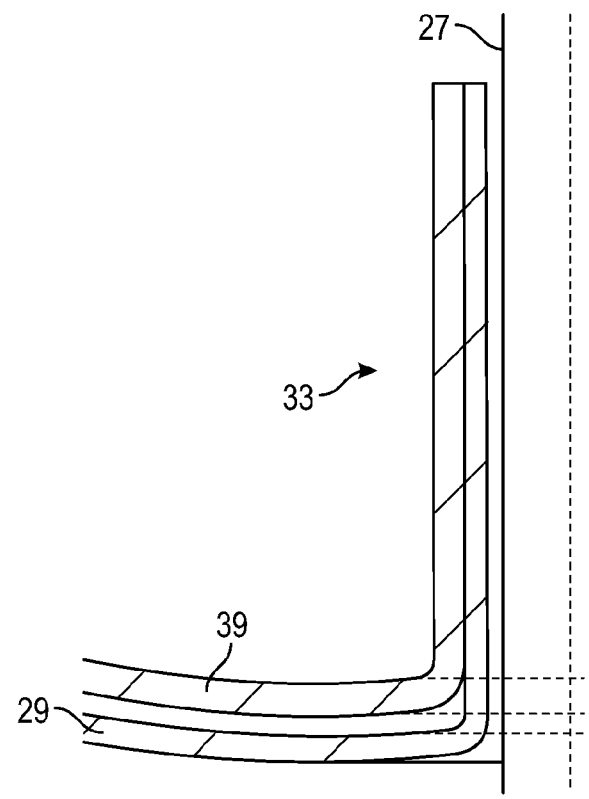
FIG. 8 is an enlarged sectional side view of a region B of the waste management appliance of FIG. 6.

Referring now to FIG. 6 of the drawings, there is depicted an enlarged cross-sectional view of a portion of the appliance 25 proximate the proximal end of the tubular body 27 with the balloon 39 fully inflated. FIGS. 7 and 8 show, respectively, enlarged sectional views of regions A and B of a proximal portion of the appliance 25 depicted in FIG. 6.

In an embodiment, the cowl 29 is formed so that it is generally C-shaped in cross section and is affixed, for example by an adhesive, to the outside of the tubular body 27 in both of locations 31 and 33 (see FIGS. 7 and 8). The balloon 39 is similarly generally C-shaped in cross-section and is affixed, for example adhered, to those parts of the cowl 29 that are adhered to the tubular body 27, and directly to the outside surface of the tubular body 27 for those parts of the cowl 29 in locations 35 that are not affixed to the tubular body 27. In this way, at the first circumferential location 31, the cowl 29 is sandwiched between the balloon 39 and the outer surface of the tubular body 27, whereas at the second circumferential location 33, the cowl 29 is sandwiched between the balloon 39 and the outer surface of the tubular body 27 apart from in those locations 35 where the cowl 29 is not affixed to the tubular body 27, at these locations 35 the balloon 39 is adhered to the outer surface of the tubular body 27.

As shown in FIG. 6, an inflation lumen 41 extends within the tubular body 27 and opens at a proximal end to the interior of the balloon 39. As described above, a source of fluid may be connected to the distal end of the lumen 41 (optionally via a valve assembly 1 of the type described above) and operated to inflate and deflate the balloon 39. FIG. 6 also shows an irrigation lumen 43 that opens proximate to the proximal end of the tubular body 27.

The appliance 25 may be assembled, for example, by affixing (for example by an adhesive) the cowl 29 to the outside of the tubular body 27 in the first circumferential location 31, affixing the balloon 39 to the cowl 29 in the first circumferential location 31, affixing the balloon 39 to the (now free) other extremity of the cowl 29, and then affixing the cowl 29 and balloon 39 (in locations 35) to the outside of the tubular body 27 in the second circumferential location 33.

At least part of the appliance 25 may be coated (inside, outside, or inside and outside) with a lubricious coating, such as parylene. In an embodiment, the tubular body 27 and the cowl 29 are coated with parylene as this aids flow of waste through the tubular body 27 (when the appliance 25 is installed in a subject) and withdrawal of the appliance 25 from a subject. In an embodiment, a proximal region of the tubular body 27 and the balloon 39 are all formed of a soft, compliant material—for example, silicone with a shore A hardness of about 70 to 100, or with a shore A hardness of about 80 to 90. The cowl 29 may also be of silicone and may have similar properties to those of the balloon 39 or the tubular body 27.

It will be appreciated that whilst various aspects and embodiments of the present invention have heretofore been described, the scope of the present invention is not limited to the particular arrangements set out herein and instead extends to encompass all arrangements, and modifications and alterations thereto, which fall within the scope of the appended claims.

For example, while the cowl 29 can be coupled to the tubular body 27 around the entire circumference (internal or external) of the tubular body 27 in the aforementioned first location 31, it will be appreciated that the cowl 29 could instead be coupled to tubular body 27 only at spaced locations around the circumference of the tubular body 27, for example at locations corresponding to the finger pockets 37.

It should also be noted that whilst the accompanying claims set out particular combinations of features described herein, the scope of the present invention is not limited to the particular combinations hereafter claimed, but instead extends to encompass any combination of features herein disclosed.

Finally, it should be noted that any element in a claim that does not explicitly state "means for" performing a specified function, or "steps for" performing a specific function, is not to be interpreted as a "means" or "step" clause as specified in 35 U.S.C. Sec. 112(f). In particular, the use of "step of" in the claims appended hereto is not intended to invoke the provisions of 35 U.S.C. Sec. 112(f).

What is claimed is:

1. A waste management appliance, comprising:
   a tubular body having a proximal end and a distal end;
   a cowl fastened to said tubular body at a first circumferential location in the vicinity of said proximal end, said cowl extending distally outside of said tubular body to a second circumferential location spaced distally from said first circumferential location, said cowl being fastened to said tubular body at said second circumferential location at a plurality of spaced positions around the circumference of said tubular body;
   an inflatable balloon provided within said cowl; and
   an inflation lumen having a proximal end opening to the interior of said balloon and extending distally towards the distal end of said tubular body;
   wherein the cowl can be separated from said tubular body at a plurality of circumferential regions where the cowl is not fastened to the tubular body to form a plurality of pockets between the cowl and the uninflated balloon, and
   the balloon can be inflated to a desired extent within the cowl by injecting a predetermined amount of fluid into said balloon via said lumen, the cowl functioning in the event of an attempt to inject more than said predetermined amount of fluid into said balloon to restrain inflation of said balloon beyond said desired extent.

2. The waste management appliance according to claim 1, wherein each of said pockets is configured to receive a finger for the purpose of guiding the balloon into a subject.

3. The waste management appliance according to claim 1, wherein said cowl is fastened to an outside surface of said tubular body at said first circumferential location.

4. The waste management appliance according to claim 1, wherein said cowl is fastened to an internal surface of said tubular body at said first circumferential location.

5. The waste management appliance according to claim 1, wherein said cowl is cut away at locations in which the cowl is not affixed to said tubular body at said second circumferential location.

6. The waste management appliance according to claim 1, wherein said cowl is sandwiched between said balloon and said tubular body at said first circumferential location.

7. The waste management appliance according to claim 1, wherein said cowl is sandwiched between said balloon and said tubular body at said plurality of spaced positions at which said cowl is fastened to said tubular body at said second circumferential location.

8. The waste management appliance according to claim 1, further comprising:
   a valve assembly fluidly coupled to the inflation lumen, the valve assembly comprising a valve body having first and second valve chambers in fluid communication with said inflation lumen, a coupling for connecting the lumen to a source of fluid being provided in said first chamber, and a pressure relief valve being provided in said second chamber;
   the valve assembly and the inflation lumen being configured such that the insertion of fluid into said lumen via said coupling from a source of fluid inflates said balloon until the balloon and lumen contain a predetermined quantity of fluid, whereupon continued insertion of fluid causes said pressure relief valve to operate and fluid to leak from the lumen via said valve instead of further inflating said balloon.

9. The waste management appliance according to claim 8, wherein said pressure relief valve comprises a valve member biased to prevent the flow of fluid from said lumen.

10. The waste management appliance according to claim 9, wherein said valve member is biased by a resilient biasing means, for example a spring.

11. The waste management appliance according to claim 9, wherein said valve member is biased by a biasing force in the region of 5 to 35 kPa.

12. The waste management appliance according to claim 1, wherein said tubular body includes an externally accessible irrigation lumen that opens proximate said proximal end of said tubular body.

13. The waste management appliance according to claim 1, further comprising a waste collection receptacle.

14. The waste management appliance according to claim 13, further comprising means for detachably mounting said receptacle to said distal end of said tubular body.

15. The waste management appliance according to claim 14, wherein said receptacle mounting means comprises a plate with an opening, and means for attaching said distal end of said tubular body to said plate, in alignment with said plate opening.

16. The waste management appliance according to claim 1, wherein at least part of said waste management appliance is provided with a lubricious coating.

17. The waste management appliance according to claim 16, wherein an internal surface of said tubular body and an external surface of said cowl includes a lubricious coating.

18. The waste management appliance according to claim 16, wherein said lubricious coating comprises parylene.

* * * * *